(12) United States Patent
Kashiwagi

(10) Patent No.: US 11,583,452 B2
(45) Date of Patent: Feb. 21, 2023

(54) PAD

(71) Applicant: Daio Paper Corporation, Ehime (JP)

(72) Inventor: Tatsuhiko Kashiwagi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 999 days.

(21) Appl. No.: 16/333,659

(22) PCT Filed: Jul. 19, 2017

(86) PCT No.: PCT/JP2017/026042
§ 371 (c)(1),
(2) Date: Mar. 15, 2019

(87) PCT Pub. No.: WO2018/061418
PCT Pub. Date: Apr. 5, 2018

(65) Prior Publication Data
US 2019/0254883 A1    Aug. 22, 2019

(30) Foreign Application Priority Data

Sep. 29, 2016   (JP) .............................. JP2016-192289

(51) Int. Cl.
*A61F 13/15*   (2006.01)
*A61F 13/49*   (2006.01)
(Continued)

(52) U.S. Cl.
CPC ................ *A61F 13/49* (2013.01); *A61F 5/44* (2013.01); *A61F 13/2034* (2013.01);
(Continued)

(58) Field of Classification Search
CPC ........ A61F 5/44; A61F 13/49; A61F 13/2034; A61F 13/53; A61F 13/532; A61F 13/534; A61F 2013/537
See application file for complete search history.

(56) References Cited

U.S. PATENT DOCUMENTS

| 2003/0083631 A1 | 5/2003 | Chen et al. |
| 2003/0097105 A1 | 5/2003 | Chen et al. |
| 2016/0206482 A1 | 7/2016 | Nishikawa et al. |

FOREIGN PATENT DOCUMENTS

| CN | 205126590 U | 4/2016 |
| EP | 2656826 | 10/2013 |

(Continued)

OTHER PUBLICATIONS

Extended European Search Report for EP 17855376.4, dated Mar. 16, 2020.

(Continued)

*Primary Examiner* — Jacqueline F Stephens
(74) *Attorney, Agent, or Firm* — Andrus Intellectual Property Law

(57) ABSTRACT

A pad capable of enhancing the fitting performance to a wearer. An absorber includes a front body portion, a back body portion, and a narrowing portion, whose width dimension is reduced, provided between the front body portion and the back body portion. A first groove extending in the front-back direction is formed in a central portion in the width direction of the absorber. A third groove extending in the width direction is formed in a central portion in the front-back direction of the narrowing portion. A second groove extending in the width direction is formed in a front side portion in the front-back direction of the narrowing portion. A fourth groove extending in the width direction is formed in a back side portion in the front-back direction of the narrowing portion.

7 Claims, 12 Drawing Sheets

(51) Int. Cl.
  *A61F 5/44*   (2006.01)
  *A61F 13/20*  (2006.01)
  *A61F 13/511*  (2006.01)
  *A61F 13/532*  (2006.01)
  *A61F 13/534*  (2006.01)
  *A61F 13/53*   (2006.01)
  *A61F 13/537*  (2006.01)

(52) U.S. Cl.
  CPC ............ *A61F 13/511* (2013.01); *A61F 13/53* (2013.01); *A61F 13/532* (2013.01); *A61F 13/534* (2013.01); *A61F 2013/53778* (2013.01)

(56) References Cited

FOREIGN PATENT DOCUMENTS

| | | | | |
|---|---|---|---|---|
| JP | 5397540 | 8/1978 | | |
| JP | 2002538849 | 11/2002 | | |
| JP | 2008183160 | 8/2008 | | |
| JP | 2011-136015 | 7/2011 | | |
| JP | 5117249 | 1/2013 | | |
| JP | 2014104094 | 6/2014 | | |
| JP | 2014117321 | 6/2014 | | |
| JP | 2016049247 | 4/2016 | | |
| WO | 0124755 | 4/2001 | | |
| WO | WO2005065611 | * | 7/2005 | ............ A61F 13/15 |
| WO | 2016148192 | 9/2016 | | |

OTHER PUBLICATIONS

International Search Report, PCT/JP2017/026041, dated Oct. 24, 2017.

* cited by examiner

FIG.9
(a)
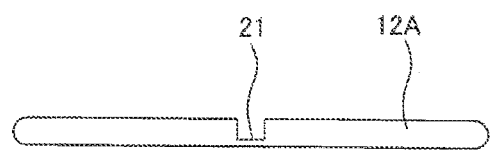
(b)
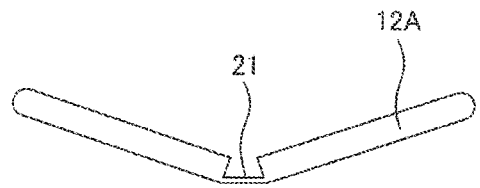

FIG.10
(a)
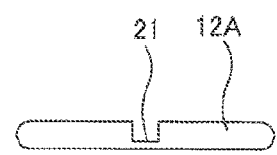
(b)
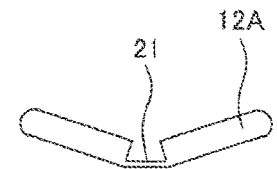

PAD

CROSS-REFERENCE TO RELATED APPLICATIONS

This application is the U.S. national stage application of International Application PCT/JP2017/026042, filed Jul. 19, 2017, which international application was published on Apr. 5, 2018, as International Publication WO 2018/061418 in the Japanese language. The International Application claims priority of Japanese Patent Application No. 2016-192289, filed Sep. 29, 2016. The international application and Japanese application are both incorporated herein by reference, in entirety.

TECHNICAL FIELD

The present invention relates to a pad to be attached to an underpants-type disposable diaper, and more particularly to a pad that can be attached in close contact with the inner surface of a disposable diaper.

BACKGROUND ART

Conventionally, it is proposed that a plurality of grooves extending in the front-back direction is formed with a predetermined interval in the width direction of an absorber, notch portions each extending toward a back side in the front-back direction are formed toward a central portion in the width direction from both side portions of a front side portion of the absorber, and notch portions each extending toward the front side in the front-back direction are formed toward a central portion in the width direction from both side portions of a back side portion of the absorber. (Patent Literature 1)

Further, it is proposed that an absorber is formed with an outer absorber and an inner absorber having a narrower width in the width direction than the outer absorber, and a plurality of grooves extending in the width direction with a predetermined interval in the front-back direction is formed to the inner side absorber. (Patent Literature 2)

CITATION LIST

Patent Literature

Patent Literature 1: JP 2014-117321 A
Patent Literature 2: JP 2014-104094 A

SUMMARY OF INVENTION

Technical Problem

However, according to the means described in Patent Literature 1, an intermediate portion in the front-back direction of an absorber cannot be easily deformed inward, and also a central portion partitioned by right and left grooves in the width direction of the absorber cannot be easily deformed inward, and therefore, there is a possibility that the absorber cannot be closely attached to the inner surface of a disposable diaper or the like and that high fitting performance cannot be obtained for a wearer.

Further, according to the means described in Patent Literature 2, both side portions in the width direction of an absorber cannot be easily deformed inward, and therefore there is a possibility that the absorber cannot be closely attached to the inner surface of a disposable diaper or the like and that high fitting performance cannot be obtained for a wearer.

It is therefore an object of the present invention to provide a pad capable of easily deforming inward the entire region in the front-back direction and the width direction of an absorber so as to be closely attached to the inner surface of a disposable diaper and the pad being capable of enhancing the fitting performance to a wearer.

Solution to Problem

Means for solving the above problems are as follows.

According to a first aspect, is provided a pad comprising a liquid-pervious front-face sheet, a liquid-impervious back-face sheet, an absorber provided between the front-face sheet and the back-face sheet, an outer sheet on an outer surface of the back-face sheet, and engagement members on both end portions in a front-back direction of the outer sheet, wherein the absorber is formed with a front body portion, a back body portion, and a narrowing portion, whose width dimension is reduced, provided between the front body portion and the back body portion, a first groove extending in a front-back direction is formed at a central portion in a width direction of the absorber, a third groove extending in the width direction is formed at a central portion in the front-back direction in the narrowing portion, a second groove extending in the width direction is formed in a front side portion in the front-back direction in the narrowing portion, and a fourth groove extending in the width direction is formed in a back side portion in the front-back direction in the narrowing portion.

According to a second aspect, in the configuration of the first aspect, the second groove is formed with a second left groove extending to a back side in the front-back direction toward a left side in the width direction from the first groove and a second right groove extending to the back side in the front-back direction toward a right side in the width direction from the first groove, and the fourth groove is formed with a fourth left groove extending to a front side in the front-back direction toward the left side in the width direction from the first groove and a fourth right groove extending to the front side in the front-back direction toward the right side in the width direction from the first groove.

According to a third aspect, in the configuration of the first or second aspect, a fifth groove is formed at a front end portion of the first groove, a sixth groove is formed at a back end portion of the first groove, the fifth groove is formed with a fifth left groove extending to the front side in the front-back direction toward the left side in the width direction from the first groove and a fifth right groove extending to the front side in the front-back direction toward the right side in the width direction from the first groove, the sixth groove is formed with a sixth left groove extending to the back side in the front-back direction toward the left side in the width direction from the first groove and a sixth right groove extending to the back side in the front-back direction toward the right side in the width direction from the first groove, a front end portion of the fifth left groove faces a left back portion of a front side engagement member, a front end portion of the fifth right groove faces a right back portion of the front side engagement member, a back end portion of the sixth left groove faces a left front portion of a back side engagement member, and a back end portion of the sixth right groove faces a right front portion of the back side engagement member.

According to a fourth aspect, in the configuration of any one of the first to third aspects, the second to fourth grooves are formed by extending from a left end to a right end in the width direction of the absorber.

According to a fifth means, in the configuration of any one of the first to fourth aspects, the second to fourth grooves are discontinuously formed.

Advantageous Effects of Invention

According to the first aspect, the absorber is formed with the front body portion, the back body portion, and the narrowing portion whose width dimension is reduced, provided between the front body portion and the back body portion, the first groove extending in the front-back direction is formed at the central portion in the width direction of the absorber, the third groove extending in the width direction is formed at the central portion in the front-back direction in the narrowing portion, the second groove extending in the width direction is formed in the front side portion in the front-back direction in the narrowing portion, and the fourth groove extending in the width direction is formed in the back side portion in the front-back direction in the narrowing portion. Therefore, the both side portions of the absorber in the width direction are deformed inward with the first groove as the center for the deforming, and the front and back portions in the front-back direction of the absorber are deformed inward with the second to fourth grooves as the center for the deforming, so that the pad can be attached to the inner surface of a disposable diaper by being close contact therewith, and the fitting performance to a wearer can be enhanced.

According to the second aspect, in addition to the effect obtained by the first aspect, the second groove has the second left groove extending to the back side in the front-back direction toward the left side in the width direction from the first groove, and the second right groove extending to the back side in the front-back direction toward the right side in the width direction from the first groove, and the fourth groove is formed with the fourth left groove extending to the front side in the front-back direction toward the left side in the width direction from the first groove and the fourth right groove extending to the front side in the front-back direction toward the right side in the width direction from the first groove. Therefore, start points from which a left front side portion positioned on the front side of the second left groove and a right front side positioned on the front side of the second right groove are deformed inward are displaced in the front-back direction, such that the left front side portion and the right front side portion can be attached further closely to an inner surface of a front body of a disposable diaper, and the fitting performance to a wearer can be further enhanced. Further, start points from a left back side portion positioned on the back side of the fourth left groove and a right back side portion positioned on the back side of the fourth right groove are deformed inward are displaced in the front-back direction, such that the left back side portion and the right back side portion can be attached closely to an inner surface of a back body of the disposable diaper, and the fitting performance to a wearer can be further enhanced.

According to the third aspect, in addition to the effect obtained by the first or second aspect, the fifth groove is formed in the front end portion of the first groove, the sixth groove is formed at the back end portion of the first groove, the fifth groove is formed with the fifth left groove extending to the front side in the front-back direction toward the left side in the width direction from the first groove and the fifth right groove extending to the front side in the front-back direction toward the right side in the width direction from the first groove, the sixth groove is formed with the sixth left groove extending to the back side in the front-back direction toward the left side in the width direction from the first groove and the sixth right groove extending to the back side in the front-back direction toward the right side from the width direction in the first groove, the front end portion of the fifth left groove faces the left back portion of the front side engagement member, the front end portion of the fifth right groove faces the right back portion of the front side engagement member, the back end portion of the sixth left groove faces the left front portion of the back side engagement member, and the back end portion of the sixth right groove faces the right front portion of the back side engagement member. Therefore, start points from which a left front end portion positioned on the front side of the fifth left groove and a right front side positioned on the front side of the fifth right groove are deformed inward are displaced in the front-back direction such that the left front end portion and the right front end portion can be attached closely to an inner surface of a waist portion of the front body of the disposable diaper, and the fitting performance to a wearer can be further enhanced. Further, start points where a left back end portion positioned on the back side of the sixth left groove and a right back portion positioned on the back side of the sixth right groove are deformed inward are displaced in the front-back direction, such that the left back end portion and the right back end portion can be attached closely to an inner surface of a waist portion of the back body of the disposable diaper, and the fitting performance to a wearer can be further enhanced.

According to the fourth aspect, in addition to the effect obtained by any one of the first to third aspects, the second to fourth grooves are formed by extending from the left end to the right end in the width direction of the absorber, so that the front and back portions in the front-back direction of the absorber are deformed inward in the entire region in the width direction with the second to fourth grooves as the center for the deforming, and the inner surface of the disposable diaper is closely attached to the entire region in the width direction of the pad, and the fitting performance to a wearer can be further enhanced.

According to the fifth aspect, in addition to the effect obtained by any one of the first to fourth aspects, since the second to fourth grooves are discontinuously formed, diffusion in the width direction of the liquid absorbed in the absorber can be suppressed to diffuse the liquid to the entire region of the absorber.

BRIEF DESCRIPTION OF DRAWINGS

FIG. 9(a) is a side view of the upper absorber taken along line B-B, and FIG. 9(b) is a side view in a state where the upper absorber is curved inward with a groove.

FIG. 10(a) is a side view of the upper absorber taken along line C-C, and FIG. 10(b) is a side view in a state where the upper absorber is curved inward with a groove.

DESCRIPTION OF EMBODIMENTS

Figure 1:
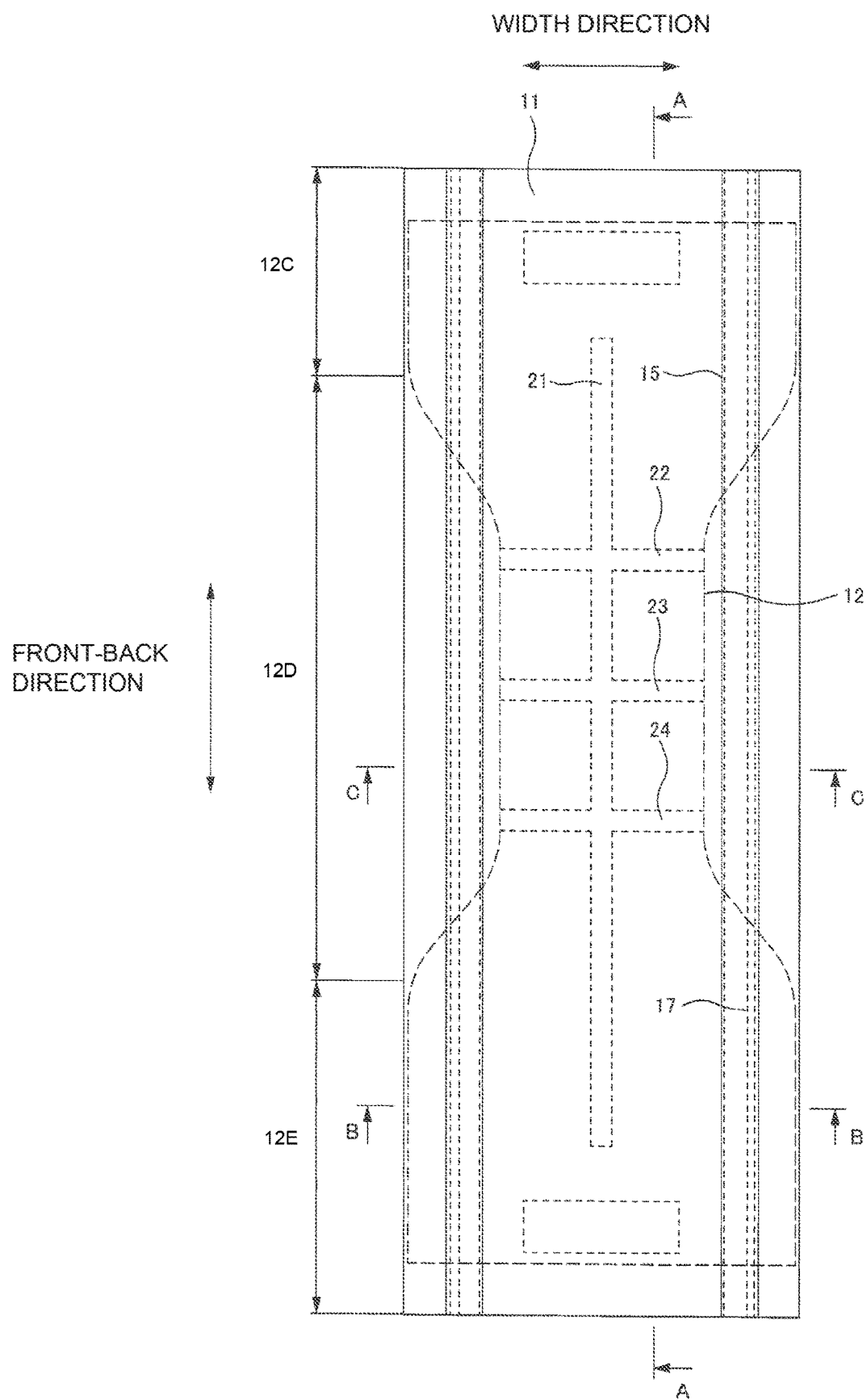
FIG. 1 is a plan view of an inner surface of a pad.

As illustrated in FIGS. 1 to 6, the pad to be mounted in an underpants-type disposable diaper includes, in order from the internal surface side positioned on the body surface side, a liquid-pervious front-face sheet 11, an absorber 12 that absorbs liquid, a liquid-impervious back-face sheet 13, an outer sheet 14 made of a nonwoven fabric or the like, and three-dimensional gathers 15 provided on both side portions in the width direction of the absorber 12.

The absorber 12 is formed of an inner absorber 12A positioned on the internal surface side and an outer absorber 12B positioned on the outer surface side. In addition, in the absorber 12, a narrowing portion 12D is formed in the substantially central portion in the longitudinal direction corresponding to the crotch portion of a wearer. For convenience, in the present specification, the front side portion in the longitudinal direction from the narrowing portion 12D in the absorber 12 corresponding to the front body of a wearer is referred to as a front body portion 12C, and the back side portion in the longitudinal direction from the narrowing portion 12D in the absorber 12 corresponding to the back body of a wearer is referred to as a back body portion 12E.

A rectangular front side engagement member 18A having a long side in the width direction is provided on an outer surface of the outer sheet 14 corresponding to a front end portion of the front body portion 12C of the absorber 12, and a rectangular back side engagement member 18B having a long side in the width direction is provided on the outer surface of the outer sheet 14 corresponding to the back end portion of the back body portion 12E of the absorber 12. The front side engagement member 18A and the back side engagement member 18B are collectively referred to as engagement members 18.

As the front-face sheet 11, a porous or nonporous nonwoven fabric, a porous plastic sheet or the like is preferable. For a raw material fiber forming the nonwoven fabric, in addition to synthetic fibers such as olefin type such as polyethylene or polypropylene, polyester type, polyamide type, etc., regenerated fibers such as rayon and cupra, and natural fibers such as cotton can be used. The nonwoven fabric can be obtained by an appropriate processing method, such as a spun lace method, a spun bond method, a thermal bond method, a melt blown method, and a needle punch method. In these processing methods, the spun lace method is excellent in terms of flexibility and drapability, and the thermal bond method is excellent in terms of bulkiness and softness. When a large number of through holes are formed on the front-face sheet 11, urine and the like are quickly absorbed, and dry touch property is excellent. Further, front and back end portions in the longitudinal direction of the front-face sheet 11 extend in the front-back direction beyond front and back end portions in the longitudinal direction of the absorber 12 and are fixed to front and back end portions in the longitudinal direction of the back-face sheet 13. Right and left end portions in the width direction of the front-face sheet 11 extend in the lateral direction of right and left end portions in the width direction of the absorber 12 and are fixed to right and left end portions in the width direction of the back-face sheet 13.

The absorber 12 is basically a known absorber, for example, accumulated bodies of pulp fibers, assembly of filaments such as cellulose acetate, or nonwoven fabrics, and as necessary, super absorbent polymers can be mixed and fixed. Further, the absorber 12 is wrapped with liquid-pervious crepe paper or the like in order to prevent super absorbent polymers or the like from falling off.

Figure 2:
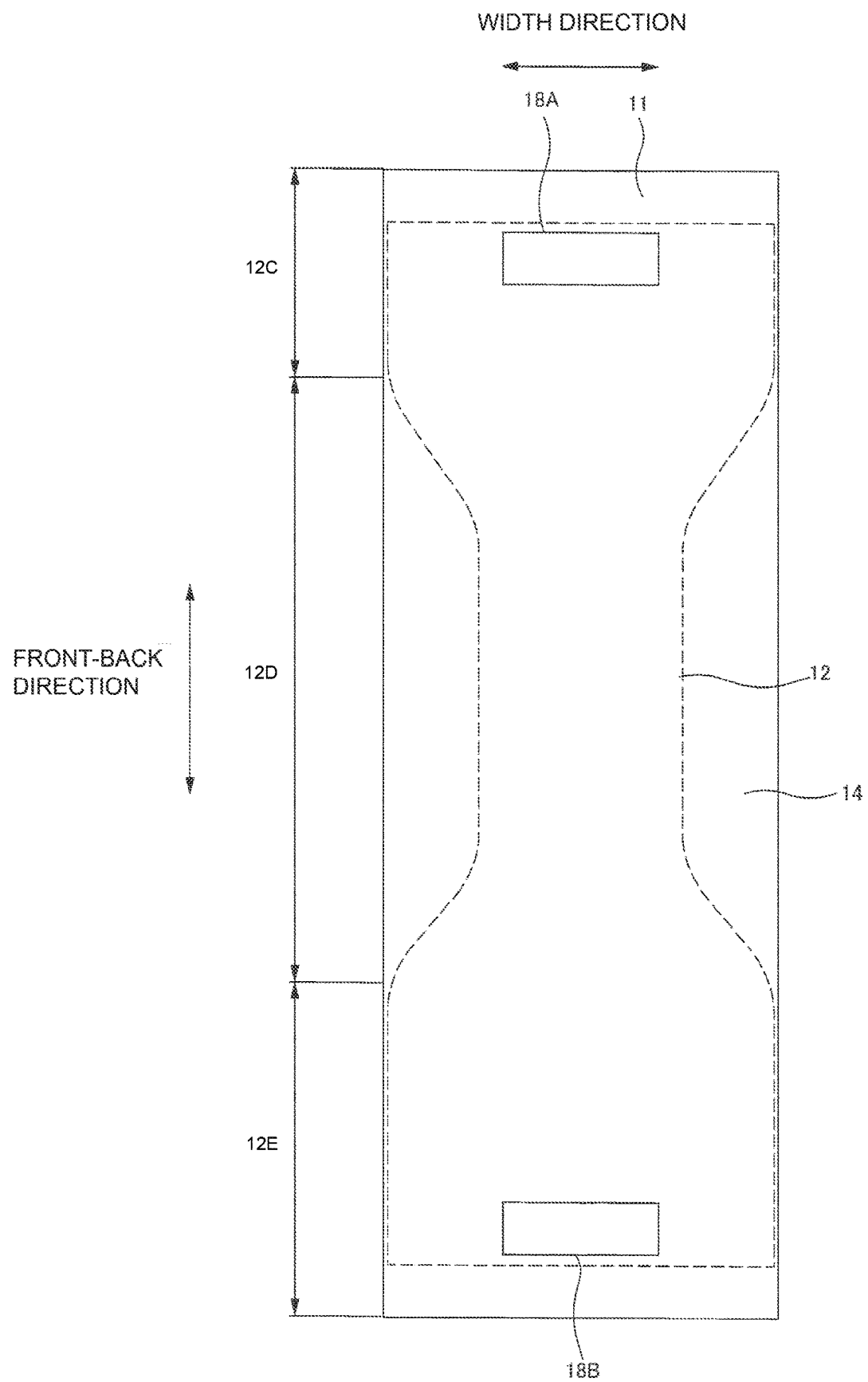
FIG. 2 is a plan view of an outer surface of the pad.
Figure 3:
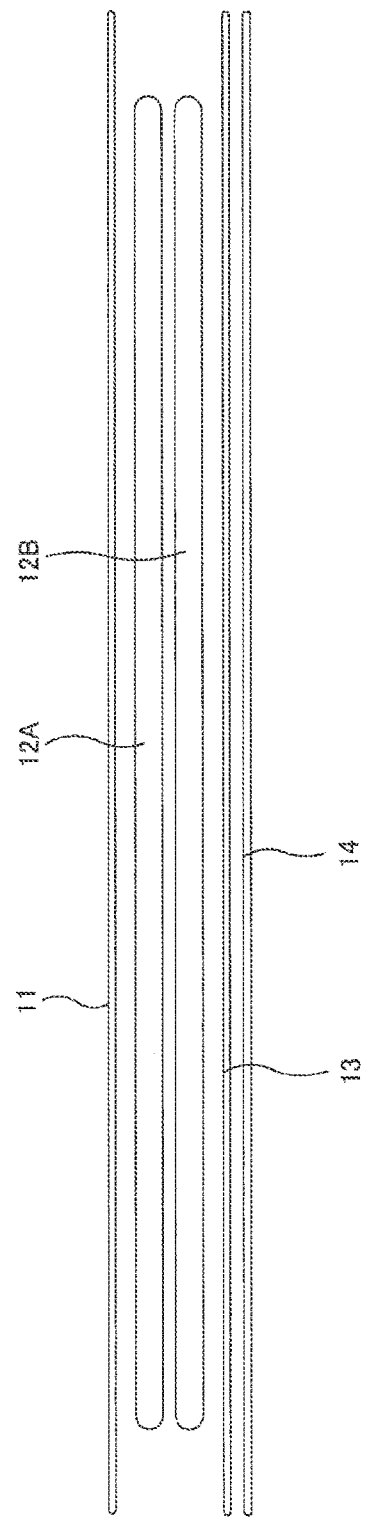
FIG. 3 is a cross-sectional view taken along line A-A of FIG. 1.
Figure 4:
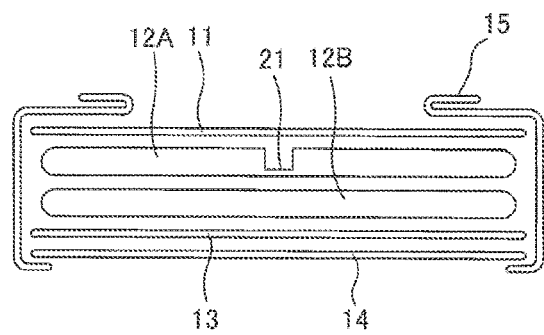
FIG. 4 is a cross-sectional view taken along line B-B of FIG. 1.
Figure 5:
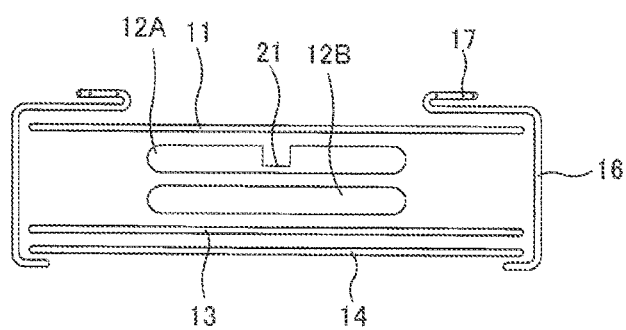
FIG. 5 is a cross-sectional view taken along a line C-C in FIG. 1.

The length in the longitudinal direction of the narrowing portion 12D is formed to be 20 to 50% in the longitudinal direction of the absorber 12, and the narrowest width in the width direction of the narrowing portion 12D is formed to be 40 to 60% of the width of the absorber 12 in the width direction. As a result, the pad can be brought into close contact with a wearer, and the fitting performance can be enhanced. FIGS. 1 and 2 illustrate a substantially hourglass-shaped absorber 12 in which the narrowing portion 12D is formed in the substantially central portion in the longitudinal direction, but the absorber may be formed in a rectangular shape or the like without forming the narrowing portion 12D. FIGS. 1 and 2 illustrate an embodiment in which the longitudinal length of the front body portion 12C is formed to be shorter than the longitudinal length of the back body portion 12E. However, the longitudinal length of the front body portion 12C and the longitudinal length of the back body portion 12E may be the same.

As the back-face sheet 13, a liquid-impermeable plastic sheet such as polyethylene sheet or polypropylene sheet is used, but in recent years, it is preferable to have moisture permeability from the standpoint of prevention of stuffiness. The waterproof/moisture pervious sheet is a microporous sheet obtained by melt kneading an olefinic resin such as polyethylene resin and polypropylene resin, and inorganic filler, forming a sheet with the kneaded materials, and then uniaxially or biaxially stretching the sheet. Further, the front and back end portions in the longitudinal direction of the back-face sheet 13 extend in the front-back direction beyond the front and back end portions in the longitudinal direction of the absorber 12 and are fixed to the front and back end portions in the longitudinal direction of the outer sheet 14. The right and left end portions in the width direction of the back-face sheet 13 extend in the lateral direction from the right and left end portions in the width direction of the absorber 12 and are fixed to the right and left end portions in the width direction of the outer sheet 14.

As the outer sheet 14, a porous or nonporous nonwoven fabric, a porous plastic sheet or the like is preferable. As material fibers constituting the nonwoven fabric, the same material fibers as the front-face sheet 11 can be used.

Each of the three-dimensional gathers 15 is formed of a fixed portion fixed to a side portion in the width direction of the outer sheet 14 and a main unit section extending from the fixed portion to a side portion of the inner surface of the front-face sheet 11 beyond a side portion in the width direction of the absorber 12 and the like. In addition, the front and back end portions of the main unit section in the longitudinal direction are fixed to the front-face sheet 11, and the central portion in the longitudinal direction of the main unit section is not fixed to the front-face sheet 11 but rises inward. The three-dimensional gather 15 is formed of a double gather sheet 16 and an elongated gather elastic member 17 extending in the longitudinal direction.

As the gather sheet 16, in addition to synthetic fibers such as olefin type such as polyethylene or polypropylene, polyester type, amide type, etc., regenerated fibers such as rayon and cupra, and natural fibers such as cotton can be used, and a nonwoven fabric obtained by an appropriate processing method, such as a spun bond method, a thermal bond method, a melt blown method, and a needle punch method can be used. In particular, to prevent stuffiness, nonwoven fabric having low basis weight and excellent in air permeability is preferably used. Further, with respect to the gather sheet 16, in order to prevent permeation of urine or the like and also to prevent irritation and improve texture to the skin (dryness), it is preferable to use a water repellent treated nonwoven fabric coated with silicone type, paraffin metal type, or alkylchromic chloride type water repellent, etc.

Figure 6:
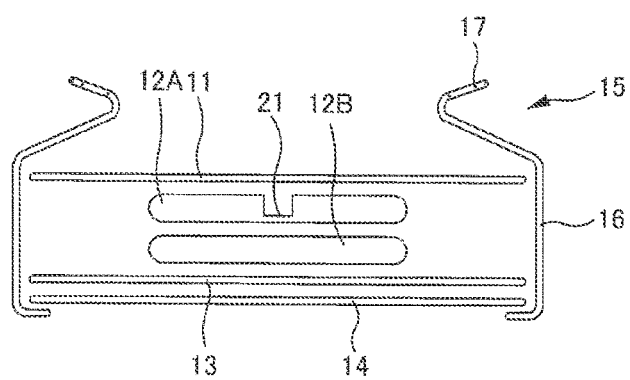
FIG. 6 is an explanatory diagram of a three-dimensional gather.

As the gather elastic member 17, materials such as styrene rubber, olefin rubber, urethane rubber, ester rubber, polyurethane, polyethylene, polystyrene, styrene butadiene, silicone, polyester, and the like which are usually used can be used. Further, in order to make it difficult to be seen from the outside, it is preferable that a fineness is set to 925 dtex or less, a stretch rate is set to 150 to 350%, and an interval is set to 10.0 mm or less. Note that, as illustrated in FIG. 6, the gather elastic member 17 makes the three-dimensional gather 15 stand inward by its stretching force, and it is also possible to use a tape-like gather having a predetermined width, in addition to a thread-like gather. Further, the stretch rate is calculated by the length at the time of stretching/the length of the natural length×100 [%].

As each of the engagement members 18, a hook member of a mechanical fastener is preferable. The hook member has (A) a check mark shape, (B) a J shape, (C) a mushroom shape, (D) a T shape, and (E) a double J shape (a J shape bonded back to back of a J shape), but may have any shape. An adhesive layer can also be used in place of the hook material.

<Pad According to First Embodiment>

Figure 7:
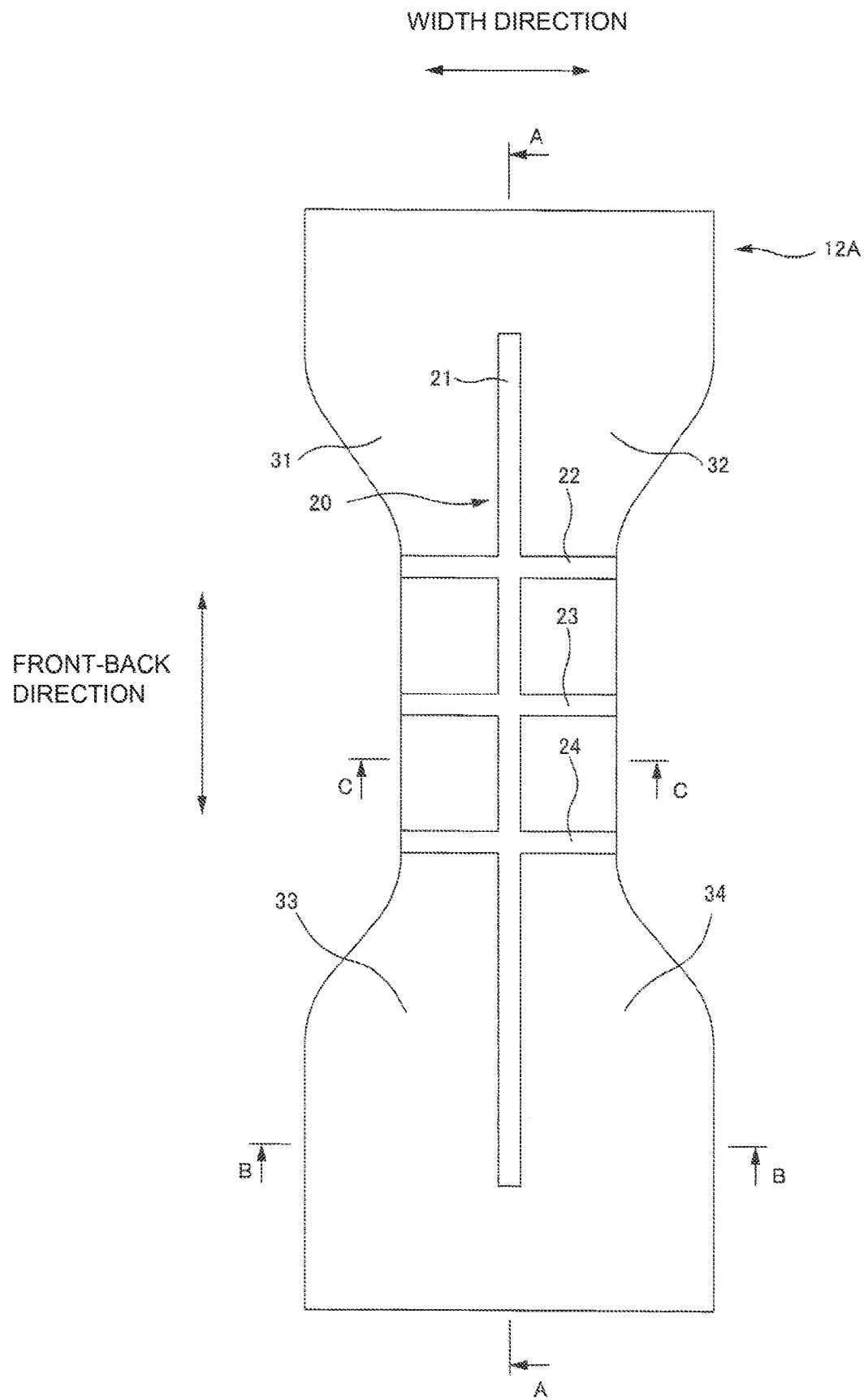
FIG. 7 is a plan view of an inner surface of an upper absorber of the first embodiment.

Next, the pad in the first embodiment will be described. As illustrated in FIG. 7, in the pad of the first embodiment, a groove 20 having a substantially concave shape in a cross-sectional view is formed on the internal surface side of the inner absorber 12A of the absorber 12. The groove 20 is formed with a first groove 21 extending in the front-back direction in the central portion in the width direction of the inner absorber 12A, a second groove 22 extending in the width direction in the front-side portion in the front-back direction of the narrowest width portion of the narrowing portion 12D, a third groove 23 extending in the width direction in the central portion in the front-back direction of the narrowest portion of the narrowing portion 12D, and a fourth groove 24 extending in the width direction in a back side portion in the front-back direction of the narrowest portion of the narrowing portion 12D.

The first groove 21 is formed so as to extend from the front body portion 12C to the back body portion 12E. A front end portion of the first groove 21 is positioned in the front body portion 12C so as to be closer to the central portion in the front-back direction than a site facing the front side engagement member 18A, and a back end portion of the first groove 21 is positioned in the back body portion 12E so as to be closer to the central portion in the front-back direction than a site facing the back side engagement member 18B.

Thereby, as illustrated in FIG. 9, in the inner absorbers 12A positioned in the front body portion 12C and the back body portion 12E, both end portions in the width direction of the inner absorber 12A are deformed inward with the first groove 21 as the center for the deforming, and both end portions in the width direction of the outer absorbers 12B positioned in the front body portion 12C and the back body portion 12E are deformed inward in conjunction with the inner absorbers 12A. As a result, the fitting performance of the pad to a wearer can be enhanced. As illustrated in FIG. 10, both end portions in the width direction of the inner absorber 12A positioned in the narrowing portion 12D are deformed inward with the first groove 21 as the center for the deforming, and both end portions in the width direction of the outer absorbers 12B positioned in the front body portion 12C and the back body portion 12E are deformed inward in conjunction with the inner absorber 12A. As a result, the fitting performance of the pad to a wearer can be enhanced.

In addition, since the liquid absorbed by the narrowing portion 12D of the inner absorber 12A is promptly diffused to the front body portion 12C and the back body portion 12E by the first groove 21, the absorption performance of the inner absorber 12A can be enhanced.

Figure 8:
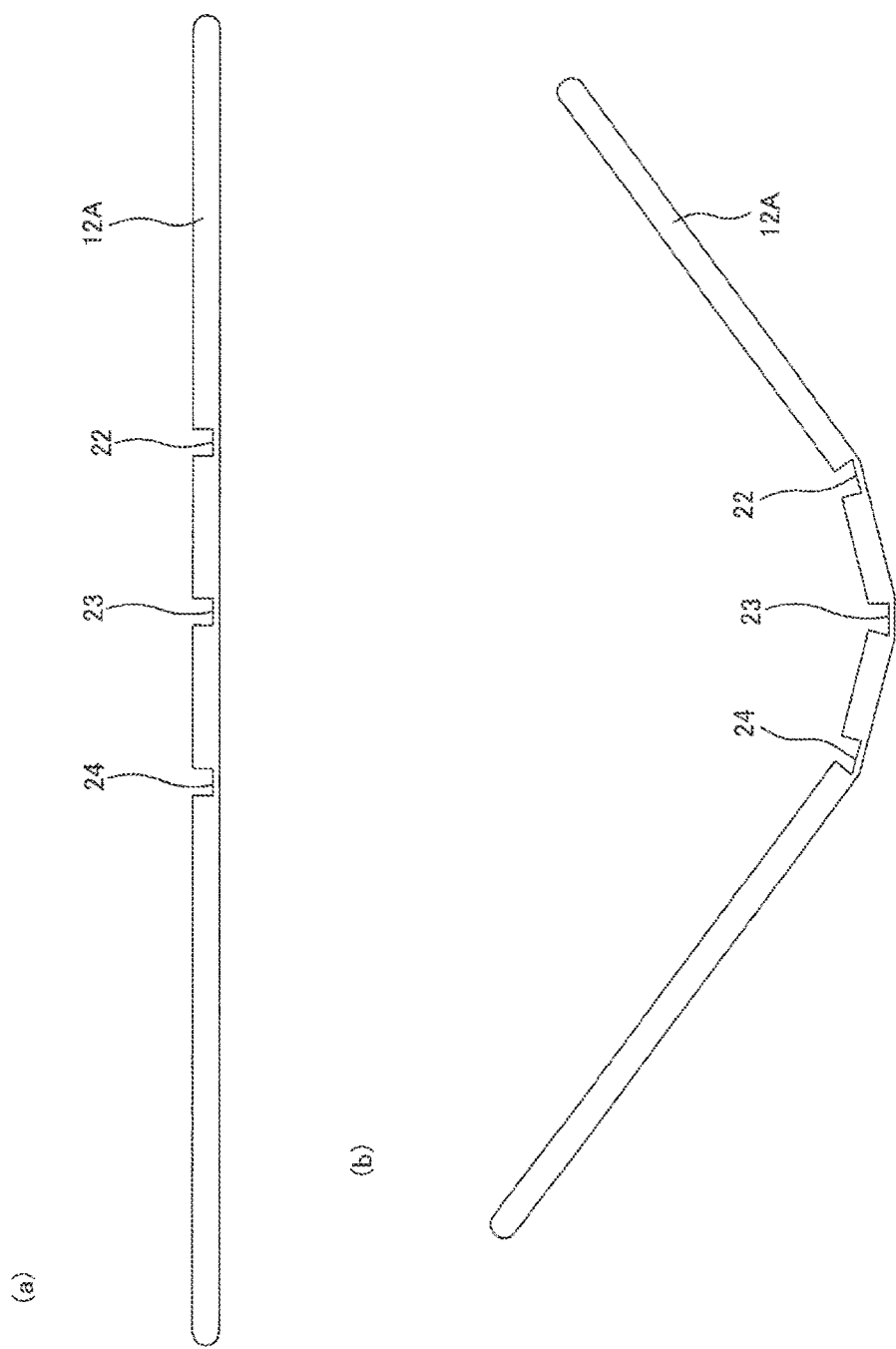
FIG. 8(a) is a side view of the upper absorber taken along line A-A.
FIG. 8(b) is a side view in a state where the upper absorber is curved inward with grooves.

The second groove 22, the third groove 23, and the fourth groove 24 extend from one side in the width direction of the narrowest portion of the narrowing portion 12D of the inner absorber 12A to the other side. Thereby, as illustrated in FIG. 8, both end portions in the front-back direction of the inner absorber 12A positioned between the second groove 22 and the fourth groove 24 in the front-back direction are deformed inward with the third groove 23 as the center for the deforming, and both end portions in the front-back direction of the outer absorber 12B positioned between the second groove 22 and the fourth groove 24 are also deformed inward in conjunction with the inner absorber 12A. The front end portion in the front-back direction of the inner absorber 12A positioned on the front side of the second groove 22 is deformed inward with the second groove 22 as the center for the deforming, and the front end portion in the front-back direction of the outer absorber 12B positioned on the front side of the second groove 22 are also deformed inward in conjunction with the inner absorber 12A. The back end portion in the front-back direction of the inner absorber 12A positioned on the back side of the fourth groove 24 in the front-back direction is deformed inward with the fourth groove 24 as the center for the deforming, and the back end portion in the front-back direction of the outer absorber 12B positioned on the back side of the fourth groove 24 is also deformed inward in conjunction with the inner absorber 12A, so that the fitting performance of the pad to a wearer can be enhanced.

Since the second groove 22, the third groove 23, and the fourth groove 24 promptly diffuse the liquid absorbed by the narrowing portion 12D of the inner absorber 12A to both side portions in the width direction of the inner absorber 12A, the absorption performance of the inner absorber 12A can be enhanced.

In FIGS. 7 to 10, the first groove 21 is formed continuously in the front-back direction with a predetermined length in the width direction, but it can also be formed discontinuously in the front-back direction. Further, each of the second groove 22 and the other grooves is continuously formed in the width direction with a predetermined length in the front-back direction, but it can also be formed discontinuously in the width direction. Although the inner surface of the inner absorber 12A is embossed to form the groove 21 and the other grooves, the amount of pulp fibers and the amount of super absorbent polymers may be reduced in sites of the inner absorber 12A where the first groove 21 and the other grooves are formed, the amount of pulp fibers and the amount of super absorbent polymers may not be arranged in sites of the inner absorber 12A where the first groove 21 and the other grooves are formed, thus, so that the first groove 21 and the other grooves are formed. Further, although the absorber 12 is formed by laminating the inner absorber 12A and the outer absorber 12B, it may be formed as a single layer.

<Pad According to Second Embodiment>

Figure 11:
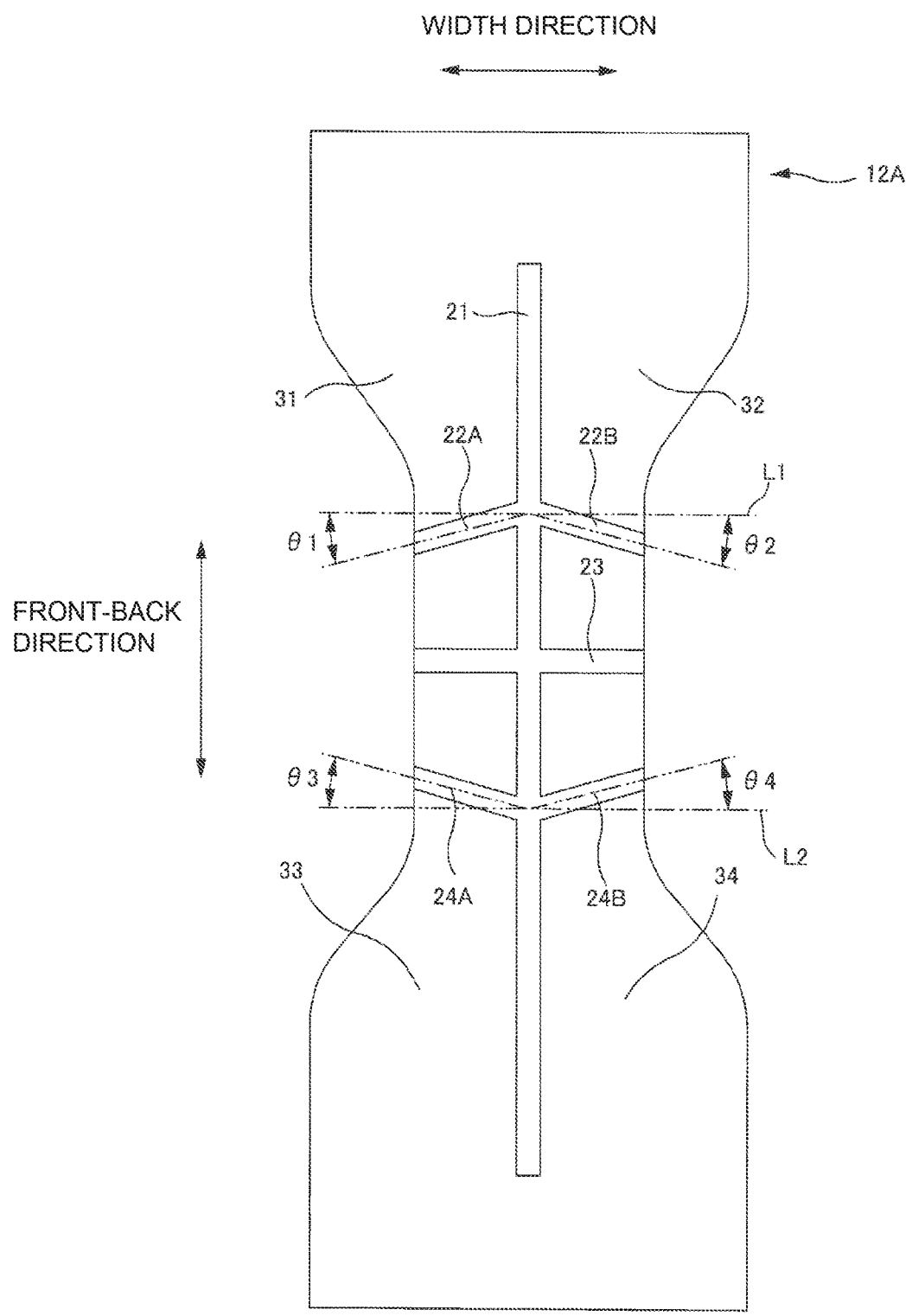
FIG. 11 is a plan view of an inner surface of an upper absorber according to a second embodiment.

Next, a pad according to a second embodiment will be described. The same parts as those of the pad according to the first embodiment are denoted by the same reference signs, and description thereof will be omitted. As illustrated in FIG. 11, the second groove 22 is formed with a second left groove 22A extending from the first groove 21 to a left end portion in the width direction of the inner absorber 12A and a second right groove 22B extending from the first groove 21 to the right end portion of the inner absorber 12A in the width direction, and the fourth groove 24 is formed with a fourth left groove 24A extending from the first groove 21 to a left end portion in the width direction of the inner absorber 12A and the fourth right groove 24B extending from the first groove 21 to the right end portion of the inner absorber 12A in the width direction.

The second left groove 22A is formed in a so-called left back inclination that extends toward the back side in the front-back direction as it extends toward the left side. In addition, the second right groove 22B is formed in a so-called right back inclination that extends toward the back side in the front-back direction as it extends toward the right side. As a result, a start point where a left front side portion 31 partitioned by the first groove 21 and the second left groove 22A of the upper absorber 12 is deformed inward is displaced in the front-back direction, such that the left front side portion 31 can be attached closely along the inner surface of an underpants-type disposable diaper. Further, a start point where a right front side portion 32 partitioned by the first groove 21 and the second right groove 22B of the upper absorber 12 is deformed inward is displaced in the front-back direction, such that the right front side portion 32 can be attached closely along the inner surface of an under pants-type disposable diaper. In addition, the outer absorber 12B is deformed inward in conjunction with the inner absorber 12A.

An intersection angle $\theta 1$ between the second left groove 22A and an imaginary line L1 extending in the width direction is formed to be 25 to 35 degrees, and an intersection angle $\theta 2$ between the second right groove 22B and the imaginary line L1 extending in the width direction is formed to be 25 to 35 degrees. Thus, the left front side portion 31 and the right front side portion 32 of the inner absorber 12A can be efficiently fitted to the front body portion of a wearer.

The fourth left groove 24A is formed in a so-called left front inclination that extends toward the front side in the front-back direction as it extends toward the left side. In addition, the fourth right groove 24B is formed in a so-called right front inclination that extends toward the front side in the front-back direction as it extends toward the right side. As a result, a start point where a left back side portion 33 partitioned by the first groove 21 and the fourth left groove 24A of the upper absorber 12 is deformed inward is displaced in the front-back direction, such that the left back side portion 33 can be attached closely along the inner surface of an underpants-type disposable diaper. Further, a start point where a right back side portion 34 partitioned by the first groove 21 and the fourth right groove 24B of the upper absorber 12 is deformed inward is displaced in the front-back direction, such that the right back side portion 34 can be attached closely along the inner surface of an underpants-type disposable diaper. In addition, the outer absorber 12B is deformed inward in conjunction with the inner absorber 12A.

An intersection angle $\theta 3$ between the fourth left groove 24A and an imaginary line L2 extending in the width direction is formed to be 25 to 35 degrees, and an intersection angle $\theta 4$ between the fourth right groove 24B and the imaginary line L2 extending in the width direction is formed to be 25 to 35 degrees. Thus, the left back side portion 33 and the right back side portion 34 of the inner absorber 12A can be efficiently fitted to the back body portion of a wearer.

<Pad According to Third Embodiment>

Figure 12:
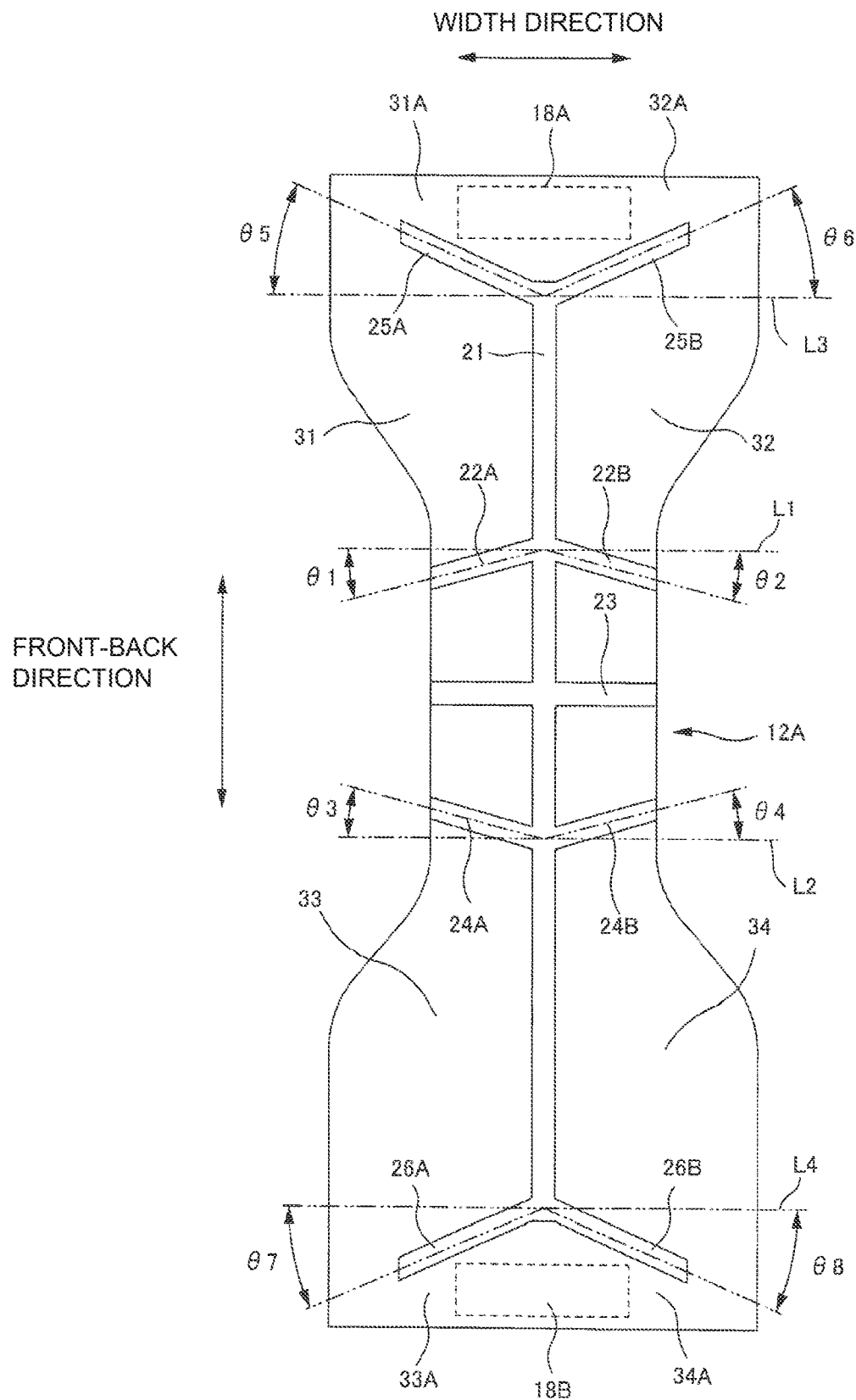
FIG. 12 is a plan view of an inner surface of an upper absorber according to a third embodiment.

Next, a pad according to a third embodiment will be described. The same parts as those of the pad according to the second embodiment are denoted by the same reference signs, and description thereof will be omitted. As illustrated in FIG. 12, the fifth groove 25 is formed in the front end portion of the first groove 21 in the front-back direction, and the sixth groove 26 is formed in the back end portion.

The fifth groove 25 is formed with a fifth left groove 25A formed so as to be inclined in the left front direction from a front end portion of the first groove 21 and a fifth right groove 25B formed so as to be inclined in the right front direction from the front end portion of the first groove 21. A left front end portion of the fifth left groove 25A faces a left side portion of the front side engagement member 18A in the front-back direction, and a right front end portion of the fifth right groove 25B faces a right side portion of the front side engagement member 18A in the front-back direction. As a result, a start point where a left front end portion 31A positioned on the front side of the fifth left groove 25A of the upper absorber 12 is deformed inward is displaced in the front-back direction, such that the left front end portion 31A can be attached closely along the inner surface of an underpants-type disposable diaper. Further, a start point where a right front end portion 32A positioned on the front side of the fifth right groove 25B of the upper absorber 12 is deformed inward is displaced in the front-back direction, such that the right front end portion 32A can be attached closely along the inner surface of an underpants-type disposable diaper. Further, deformation of the vicinity of the front side engagement member 18A is suppressed, and the front side engagement member 18A is not curved. As a result, a pad is efficiently attached to the inner surface of an underpants-type disposable diaper via the front side engagement member 18A.

An intersection angle $\theta 5$ between the fifth left groove 25A and an imaginary line L3 extending in the width direction is formed to be 25 to 35 degrees, and an intersection angle $\theta 6$ between the fifth right groove 25B and the imaginary line L3 extending in the width direction is formed to be 25 to 35 degrees. Thus, the left front end portion 31A and the right front end portion 32A of the inner absorber 12A can be efficiently fitted to the front body portion of the waist portion of a wearer. It is preferable that a left end portion of the fifth left groove 25A is formed so as to further extend toward the left side than the left end portion of the second left groove 22A in the width direction, and a right end portion of the fifth right groove 25B is formed so as to further extend toward the right side than the right end portion of the second right groove 22B in the width direction. Further, the fifth left groove 25A and the fourth left groove 24A may be formed in parallel, and the fifth right groove 25B and the fourth right groove 24B may be formed in parallel.

The sixth groove 26 is formed with a sixth left groove 26A formed so as to be inclined in the left back direction from the back end portion of the first groove 21, and a sixth right groove 26B formed so as to be inclined in the right back direction from the back end portion of the first groove 21. A left back end portion of the sixth left groove 26A faces the left side portion of the back side engagement member 18B in the front-back direction, and a right back end portion of the sixth right groove 26B faces the right side portion of the back side engagement member 18B in the front-back direction. As a result, a start point where a left back end portion 33A positioned on the back side of the sixth left groove 26A of the upper absorber 12 is deformed inward is displaced in the front-back direction, such that the left back end portion 33A can be attached closely along the inner surface of an underpants-type disposable diaper. Further, a start point where a right back end portion 34A positioned on the back side of the sixth right groove 26B of the upper absorber 12 is deformed inward is displaced in the front-back direction, such that the right back end portion 34A can be attached closely along the inner surface of an underpants-type disposable diaper. Further, deformation of the vicinity of the back side engagement member 18B is suppressed, and the back side engagement member 18B is not curved. As a result, a pad is efficiently attached to the inner surface of an underpants-type disposable diaper via the back side engagement member 18B.

An intersection angle θ7 between the sixth left groove 26A and an imaginary line L4 extending in the width direction is formed to be 25 to 35 degrees, and an intersection angle θ6 between the sixth right groove 26B and the imaginary line L4 extending in the width direction is formed to be 25 to 35 degrees. Thus, the left back end portion 33A and the right back end portion 34A of the inner absorber 12A can be efficiently fitted to the back body portion of the waist portion of a wearer. It is preferable that a left end portion of the sixth left groove 26A is formed so as to further extend toward the left side than the left end portion of the fourth left groove 24A in the width direction, and a right end portion of the sixth right groove 26B is formed so as to further extend toward the right side than the right end portion of the fourth right groove 24B in the width direction. Further, the sixth left groove 26A and the second left groove 22A may be formed in parallel, and the sixth right groove 26B and the second right groove 22B may be formed in parallel.

INDUSTRIAL APPLICABILITY

The present invention is applicable to a pad to be attached to the inner surface of a disposable diaper.

REFERENCE SIGNS LIST 11 front-face sheet
12 absorber
12C front body portion
12D narrowing portion
12E back body portion
13 back-face sheet
14 outer sheet
18 engagement members
21 first groove
22 second groove
22A second left groove
22B second right groove
23 third groove
24 fourth groove
24A fourth left groove
24B fourth right groove
25 fifth groove
25A fifth left groove
25B fifth right groove
26 sixth groove
26A sixth left groove
26B sixth right groove

The invention claimed is:

1. A pad comprising a liquid-pervious front-face sheet, a liquid-impervious back-face sheet, an absorber provided between the front-face sheet and the back-face sheet, an outer sheet on an outer surface of the back-face sheet, and engagement members on both end portions in a front-back direction of the outer sheet, wherein
the absorber is formed with a front body portion, a back body portion, and a narrowing portion, whose width dimension is reduced, provided between the front body portion and the back body portion,
a first groove extending in a front-back direction is formed at a central portion in a width direction of the absorber, a third groove extending in the width direction is formed at a central portion in the front-back direction in the narrowing portion, a second groove extending in the width direction is formed in a front side portion in the front-back direction in the narrowing portion, and a fourth groove extending in the width direction is formed in a back side portion in the front-back direction in the narrowing portion,
the second groove is formed with a second left groove extending to a back side in the front-back direction toward a left side in the width direction from the first groove and a second right groove extending to the back side in the front-back direction toward a right side in the width direction from the first groove, and
the fourth groove is formed with a fourth left groove extending to a front side in the front-back direction toward the left side in the width direction from the first groove and a fourth right groove extending to the front side in the front-back direction toward the right side in the width direction from the first groove.

2. The pad according to claim 1, wherein
a fifth groove is formed at a front end portion of the first groove,
a sixth groove is formed at a back end portion of the first groove,
the fifth groove is formed with a fifth left groove extending to the front side in the front-back direction toward the left side in the width direction from the first groove and a fifth right groove extending to the front side in the front-back direction toward the right side in the width direction from the first groove,
the sixth groove is formed with a sixth left groove extending to the back side in the front-back direction toward the left side in the width direction from the first groove and a sixth right groove extending to the back side in the front-back direction toward the right side in the width direction from the first groove,
a front end portion of the fifth left groove faces a left back portion of a front side engagement member,
a front end portion of the fifth right groove faces a right back portion of the front side engagement member,
a back end portion of the sixth left groove faces a left front portion of a back side engagement member, and
a back end portion of the sixth right groove faces a right front portion of the back side engagement member.

3. The pad according to claim 1, wherein the second to fourth grooves are formed by extending from a left end to a right end in the width direction of the absorber.

4. The pad according to claim 1, wherein the second to fourth grooves are discontinuously formed.

5. A pad comprising a liquid-pervious front-face sheet, a liquid-impervious back-face sheet, an absorber provided between the front-face sheet and the back-face sheet, an outer sheet on an outer surface of the back-face sheet, and engagement members on both end portions in a front-back direction of the outer sheet, wherein the absorber is formed with a front body portion, a back body portion, and a narrowing portion, whose width dimension is reduced, provided between the front body portion and the back body portion, a first groove extending in a front-back direction is formed at a central portion in a width direction of the absorber, a third groove extending in the width direction is formed at a central portion in the front-back direction in the narrowing portion, a second groove extending in the width direction is formed in a front side portion in the front-back direction in the narrowing portion, and a fourth groove extending in the width direction is formed in a back side portion in the front-back direction in the narrowing portion, a fifth groove is formed at a front end portion of the first groove, a sixth groove is formed at a back end portion of the first groove, the fifth groove is formed with a fifth left groove extending to the front side in the front-back direction toward the left side in the width direction from the first groove and a fifth right groove extending to the front side in the front-back direction toward the right side in the width direction from the first groove, the sixth groove is formed with a sixth left groove extending to the back side in the front-back direction toward the left side in the width direction from the first groove and a sixth right groove extending to the back side in the front-back direction toward the right side in the width direction from the first groove, a front end portion of the fifth left groove faces a left back portion of a front side engagement member, a front end portion of the fifth right groove faces a right back portion of the front side engagement member, a back end portion of the sixth left groove faces a left front portion of a back side engagement member, and a back end portion of the sixth right groove faces a right front portion of the back side engagement member.

6. The pad according to claim 5, wherein the second to fourth grooves are formed by extending from a left end to a right end in the width direction of the absorber.

7. The pad according to claim 5, wherein the second to fourth grooves are discontinuously formed.

* * * * *